(12) United States Patent
Ealovega et al.

(10) Patent No.: US 11,957,321 B2
(45) Date of Patent: Apr. 16, 2024

(54) URINE-SPECIMEN COLLECTION, STORAGE, AND TESTING DEVICE

(71) Applicants: George Ealovega, Sebastian, FL (US); Elizabeth Hatz, Port St. Lucie, FL (US)

(72) Inventors: George Ealovega, Sebastian, FL (US); Elizabeth Hatz, Port St. Lucie, FL (US)

(73) Assignee: GLR Medical Innovations, LLC, Polk City, FL (US)

( * ) Notice: Subject to any disclaimer, the term of this patent is extended or adjusted under 35 U.S.C. 154(b) by 985 days.

(21) Appl. No.: 16/811,388

(22) Filed: Mar. 6, 2020

(65) Prior Publication Data
US 2020/0323519 A1     Oct. 15, 2020

Related U.S. Application Data

(60) Division of application No. 15/644,296, filed on Jul. 7, 2017, now Pat. No. 10,582,913, which is a continuation-in-part of application No. 14/557,791, filed on Dec. 2, 2014, now abandoned.

(60) Provisional application No. 61/963,459, filed on Dec. 5, 2013.

(51) Int. Cl.
| | |
|---|---|
| *A61B 10/00* | (2006.01) |
| *A61F 2/00* | (2006.01) |
| *A61F 5/44* | (2006.01) |
| *A61F 5/451* | (2006.01) |
| *A61F 5/455* | (2006.01) |

(52) U.S. Cl.
CPC ........ *A61B 10/007* (2013.01); *A61B 10/0096* (2013.01); *A61F 5/4405* (2013.01); *A61F 5/4553* (2013.01); *A61F 2/0009* (2013.01); *A61F 5/451* (2013.01); *A61F 5/455* (2013.01)

(58) Field of Classification Search
CPC . A61B 10/007; A61B 10/0096; A61F 5/4405; A61F 5/4553; A61F 2/0009; A61F 5/451; A61F 5/455
See application file for complete search history.

(56) References Cited

U.S. PATENT DOCUMENTS

| | | | |
|---|---|---|---|
| 3,683,914 A | 8/1972 | Crowley | |
| 3,722,503 A * | 3/1973 | Hovick | A61F 5/44 4/144.3 |
| 3,776,235 A | 12/1973 | Ratcliffe et al. | |
| 3,941,699 A | 3/1976 | Ayres | |

(Continued)

FOREIGN PATENT DOCUMENTS

| | | | |
|---|---|---|---|
| BE | 899342 A * | 7/1984 | A61F 5/455 |
| DE | 19619597 A1 * | 11/1997 | A61F 5/451 |

(Continued)

*Primary Examiner* — Sean P Dougherty
(74) *Attorney, Agent, or Firm* — Perman & Green, LLP

(57) ABSTRACT

A female urinary device including a urine stream collection container having a discharge opening and a stream collection opening, the stream collection opening being configured to surround and isolate a urethral opening, an internal baffle that cooperates with at least a urine sample container to provide a spillway to the discharge opening, where the spillway provides urine passage to a collection tank, and a probe configured for interior engagement with a vaginal opening for placement of the stream collection opening relative to the urethra opening.

13 Claims, 11 Drawing Sheets

(56) References Cited

U.S. PATENT DOCUMENTS

| | | | |
|---|---|---|---|
| 4,246,901 A * | 1/1981 | Frosch | A61F 5/455 4/144.3 |
| 4,492,258 A | 1/1985 | Lichtenstein et al. | |
| 4,494,581 A | 1/1985 | Gordon | |
| 4,563,183 A | 1/1986 | Barrodale et al. | |
| 4,610,675 A * | 9/1986 | Triunfol | A61F 5/455 4/144.3 |
| 4,799,928 A | 1/1989 | Crowley | |
| 4,889,533 A * | 12/1989 | Beecher | A61F 5/4407 604/355 |
| 4,911,698 A * | 3/1990 | Wapner | A61B 10/007 4/144.3 |
| 5,147,301 A * | 9/1992 | Ruvio | A61F 5/455 604/97.02 |
| 5,257,984 A | 11/1993 | Kelley | |
| 5,511,557 A | 4/1996 | Hazard et al. | |
| 6,428,521 B1 | 8/2002 | Droll | |
| 2002/0131902 A1 | 9/2002 | Levy | |
| 2004/0162535 A1 * | 8/2004 | Preston | A61F 5/455 604/329 |
| 2005/0082290 A1 | 4/2005 | Fask et al. | |
| 2007/0025886 A1 | 2/2007 | Yong | |
| 2008/0251490 A1 | 10/2008 | Livingston et al. | |
| 2011/0028922 A1 * | 2/2011 | Kay | A61F 5/455 604/329 |
| 2011/0094319 A1 | 4/2011 | Yong | |
| 2014/0316381 A1 * | 10/2014 | Reglin | A61F 5/4553 604/544 |
| 2015/0157300 A1 | 6/2015 | Ealovega et al. | |

FOREIGN PATENT DOCUMENTS

| | | | | |
|---|---|---|---|---|
| GB | 2520970 A * | 6/2015 | | A61B 10/007 |
| WO | WO-2005107602 A1 * | 11/2005 | | A61B 10/007 |
| WO | WO-2011014739 A1 * | 2/2011 | | A61F 5/443 |

* cited by examiner

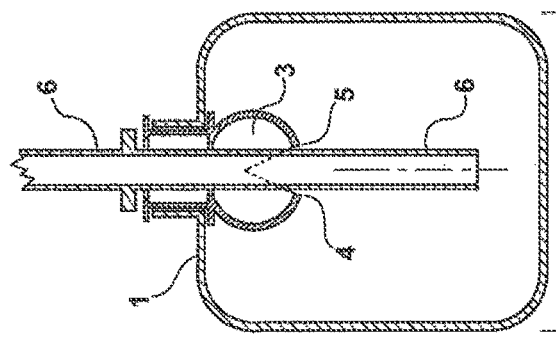
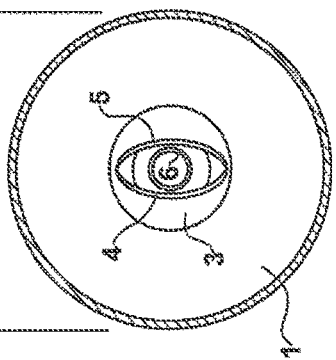
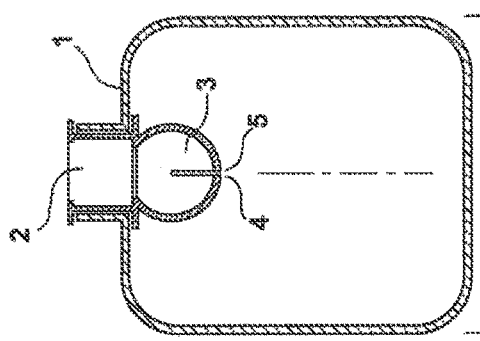
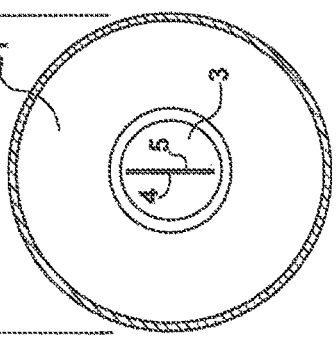
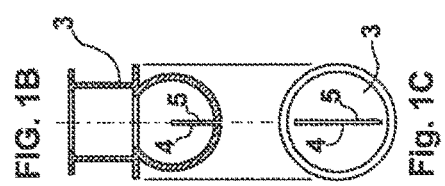
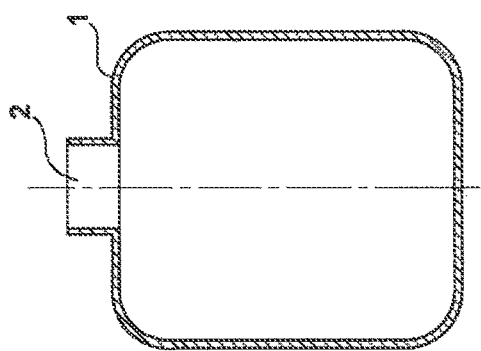

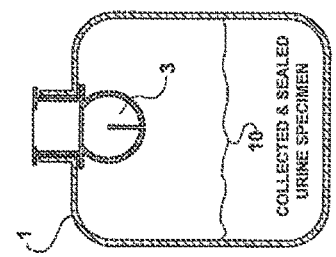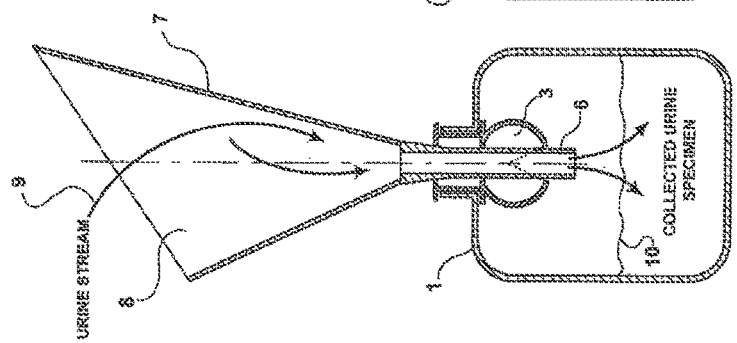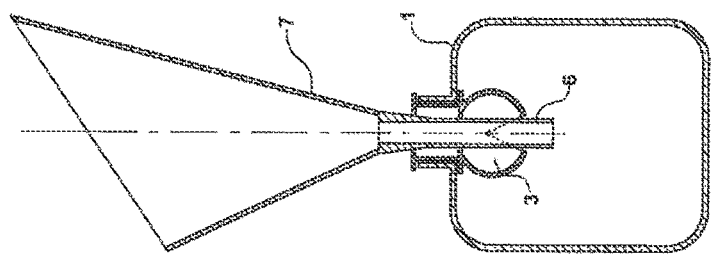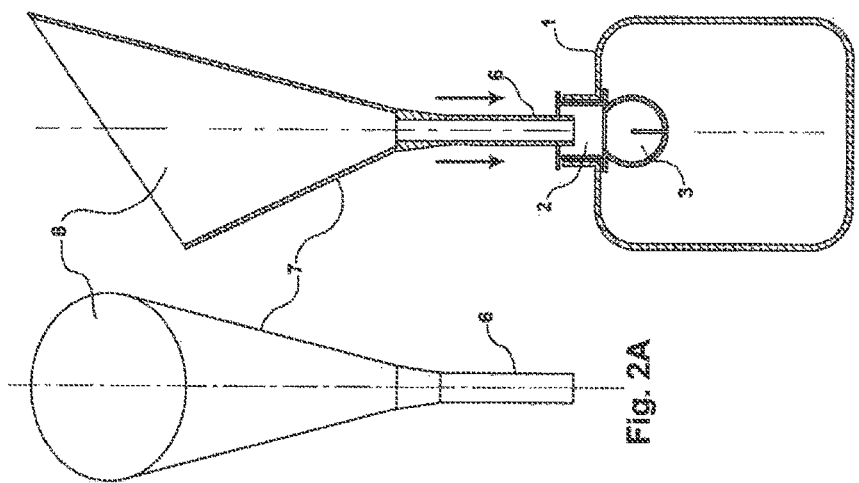

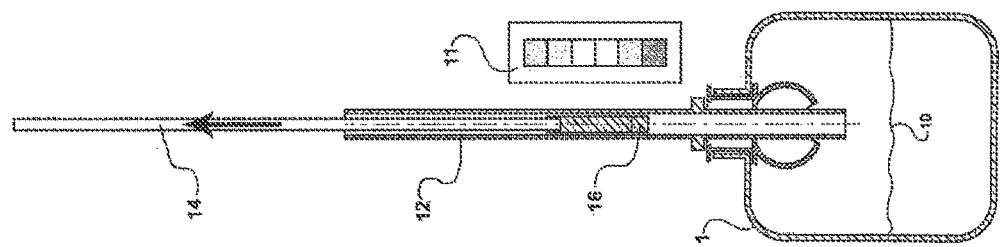
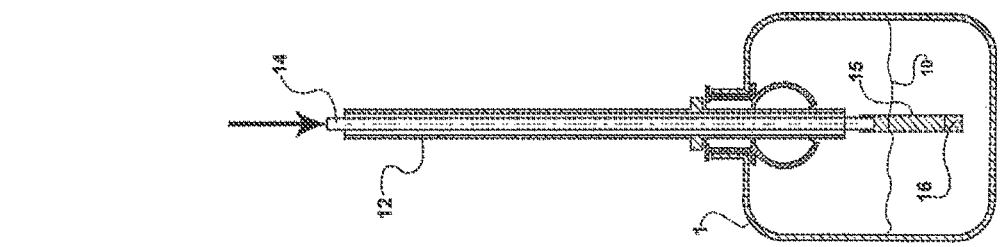
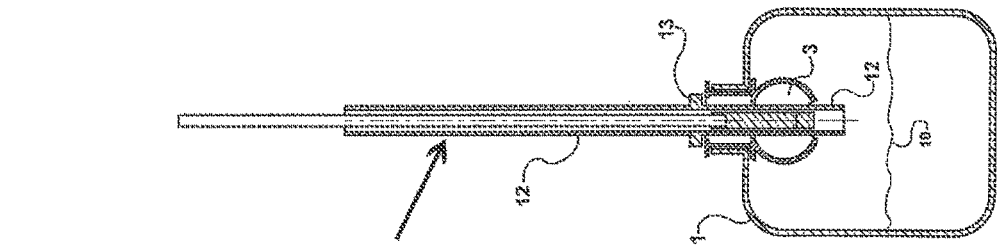
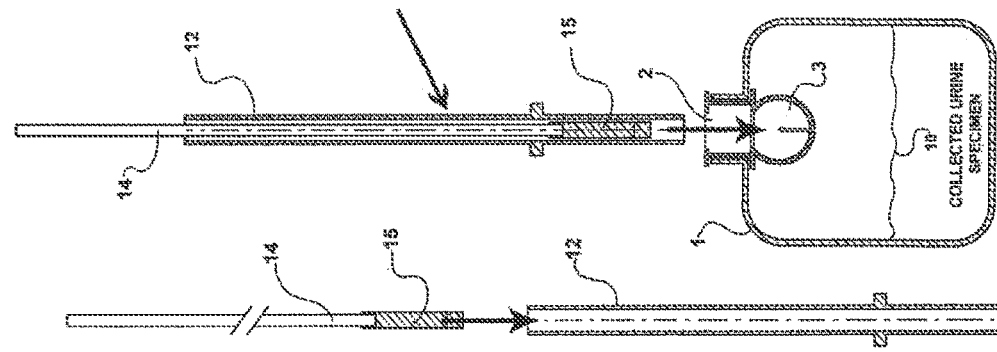
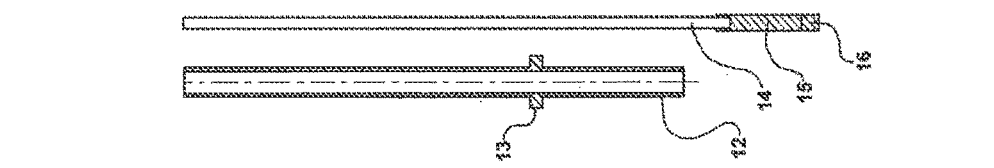

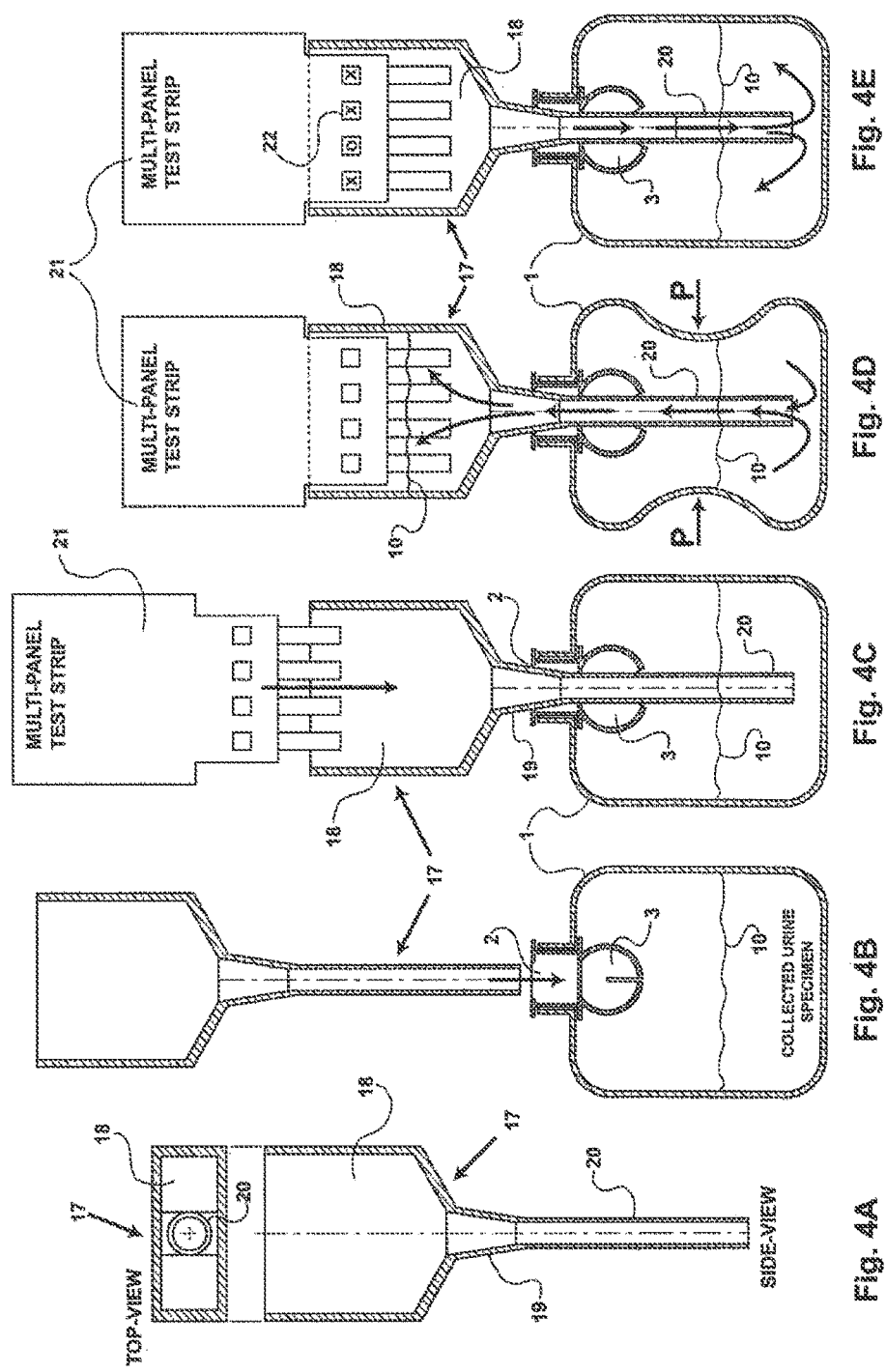

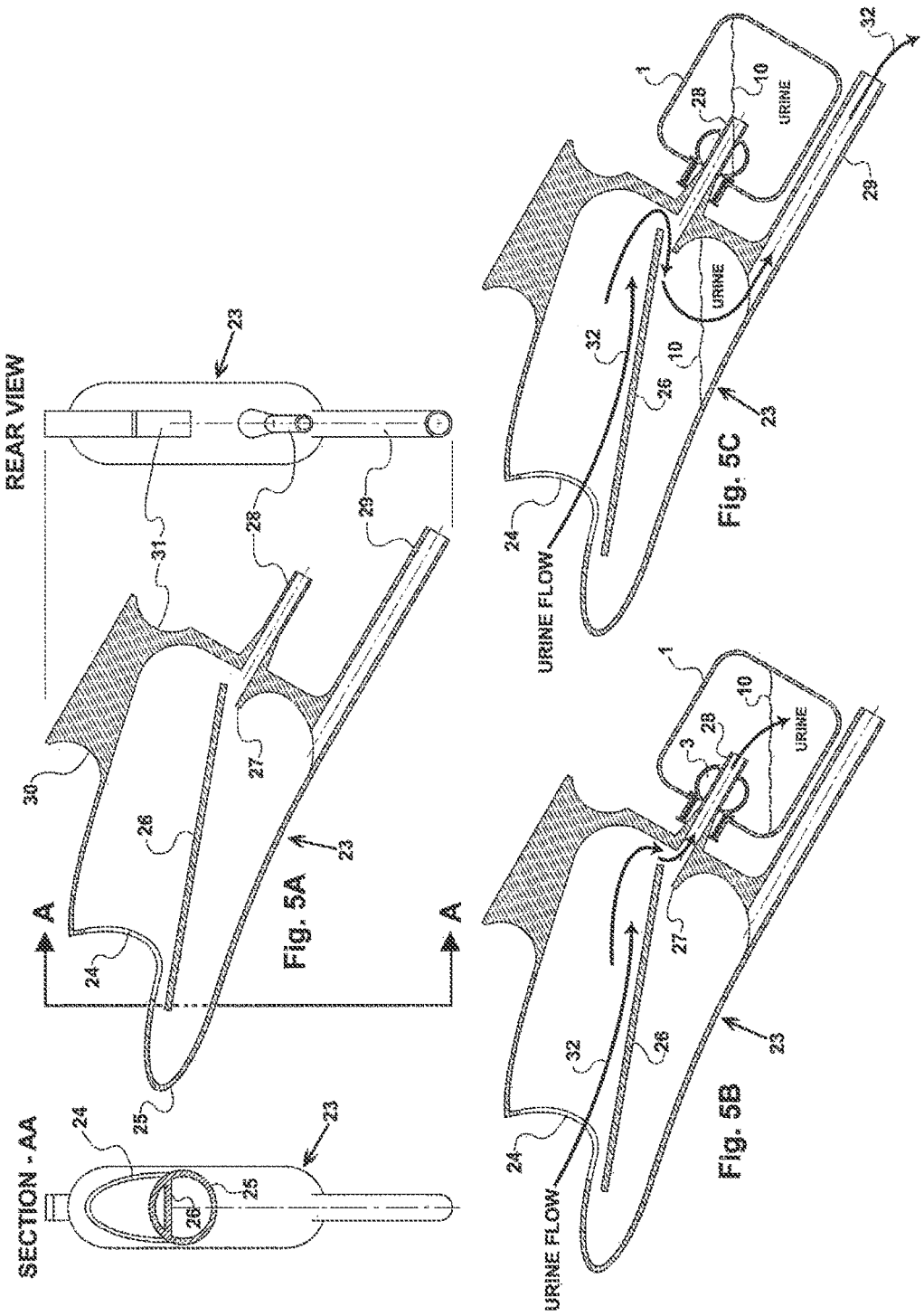

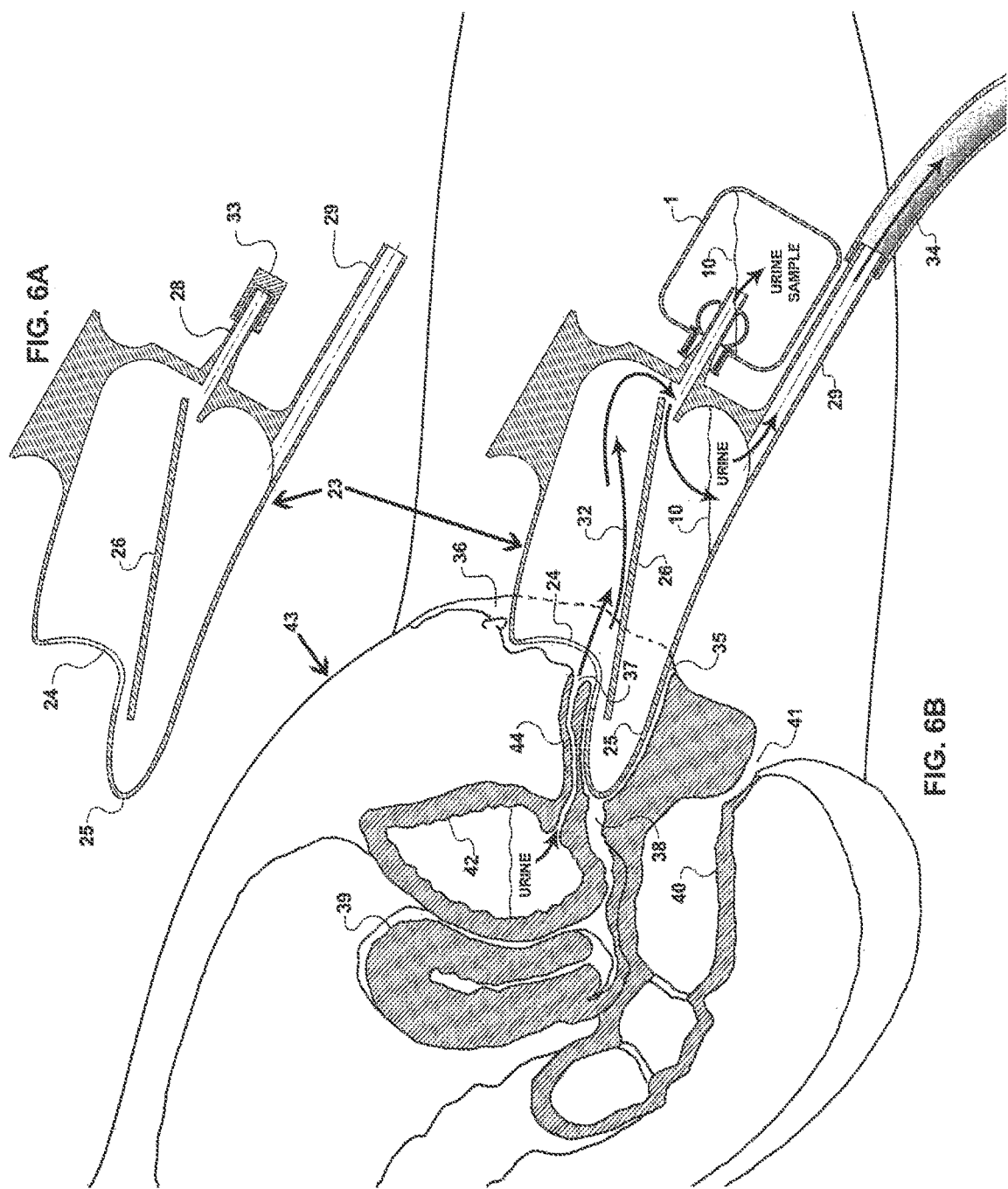

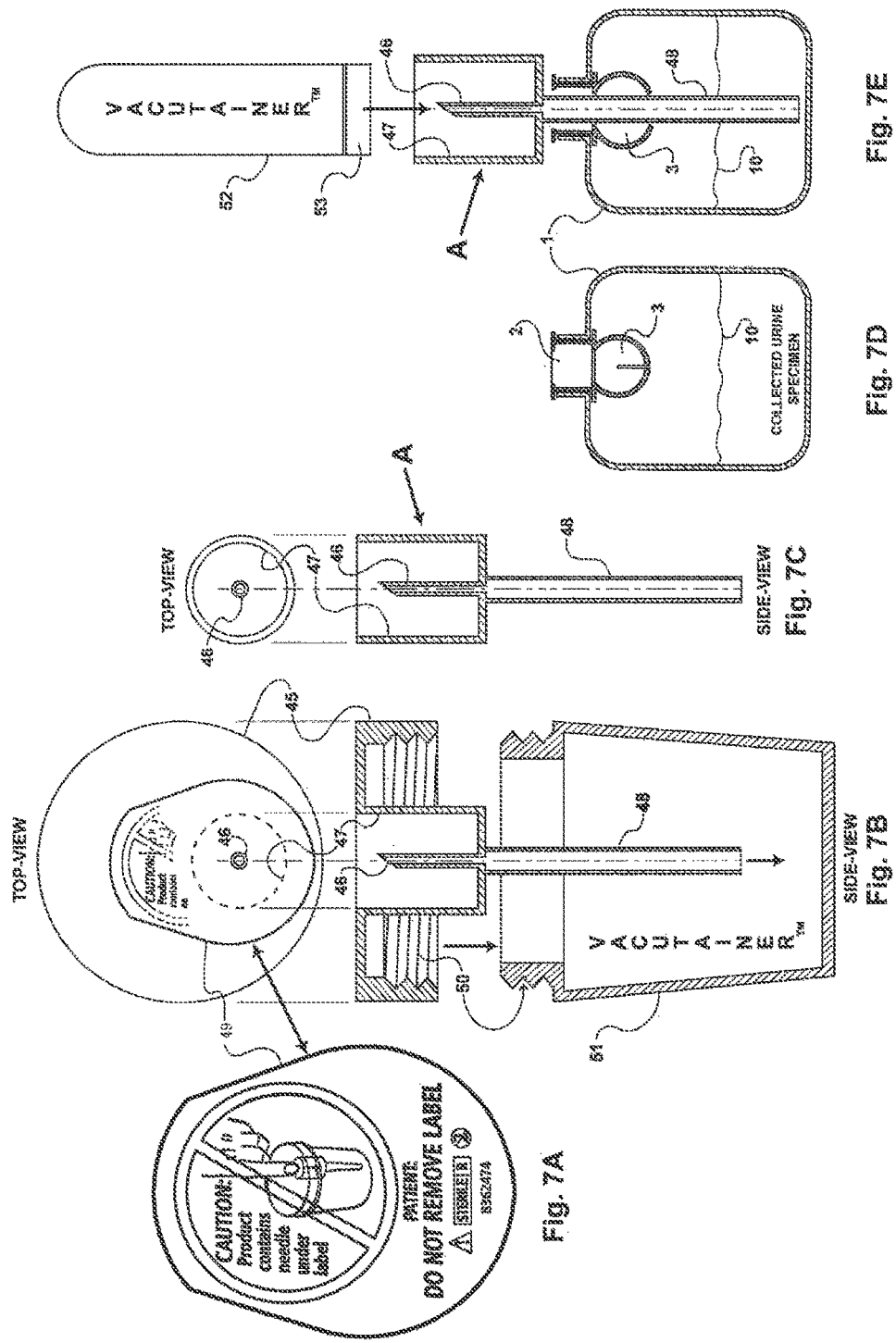

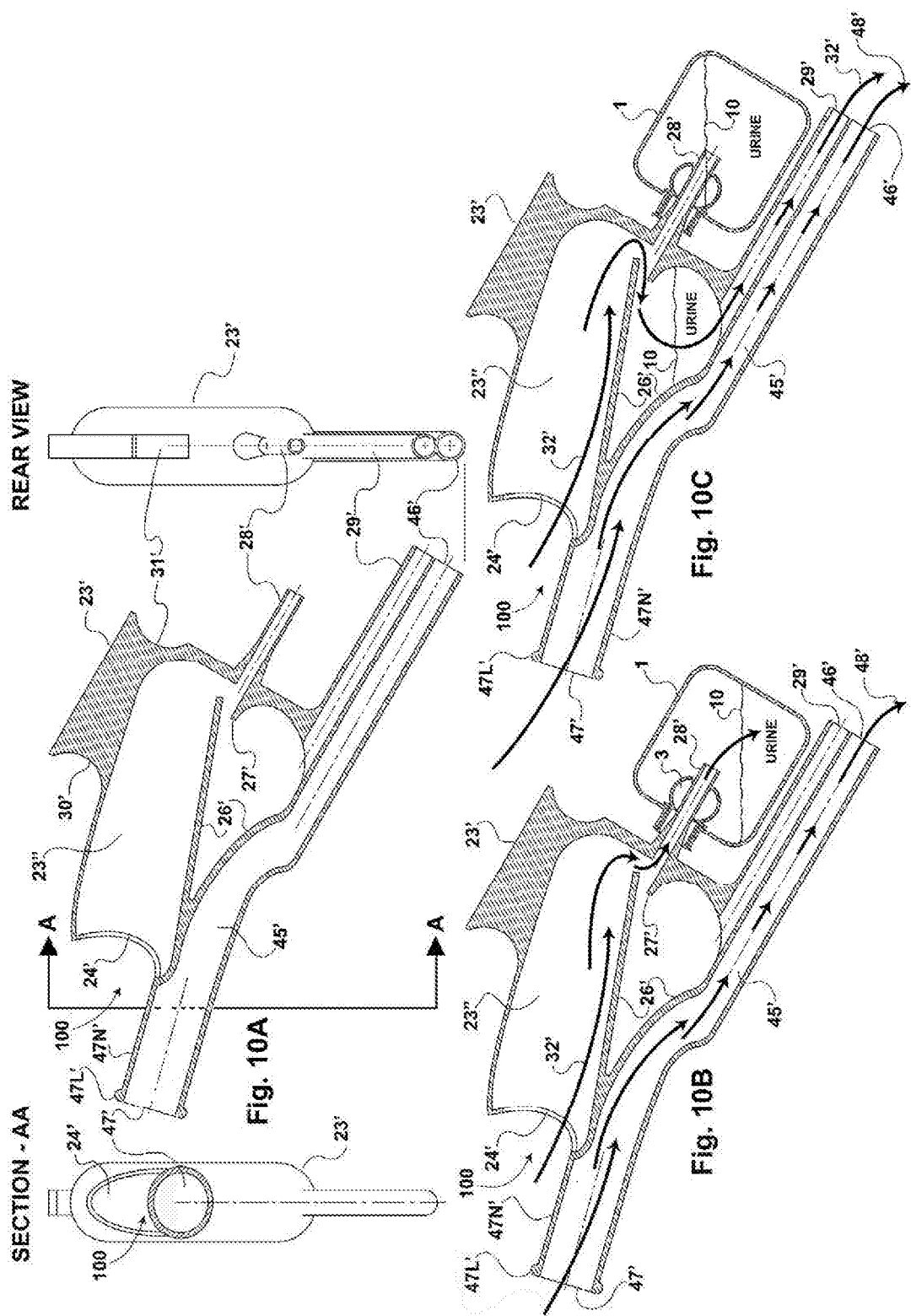

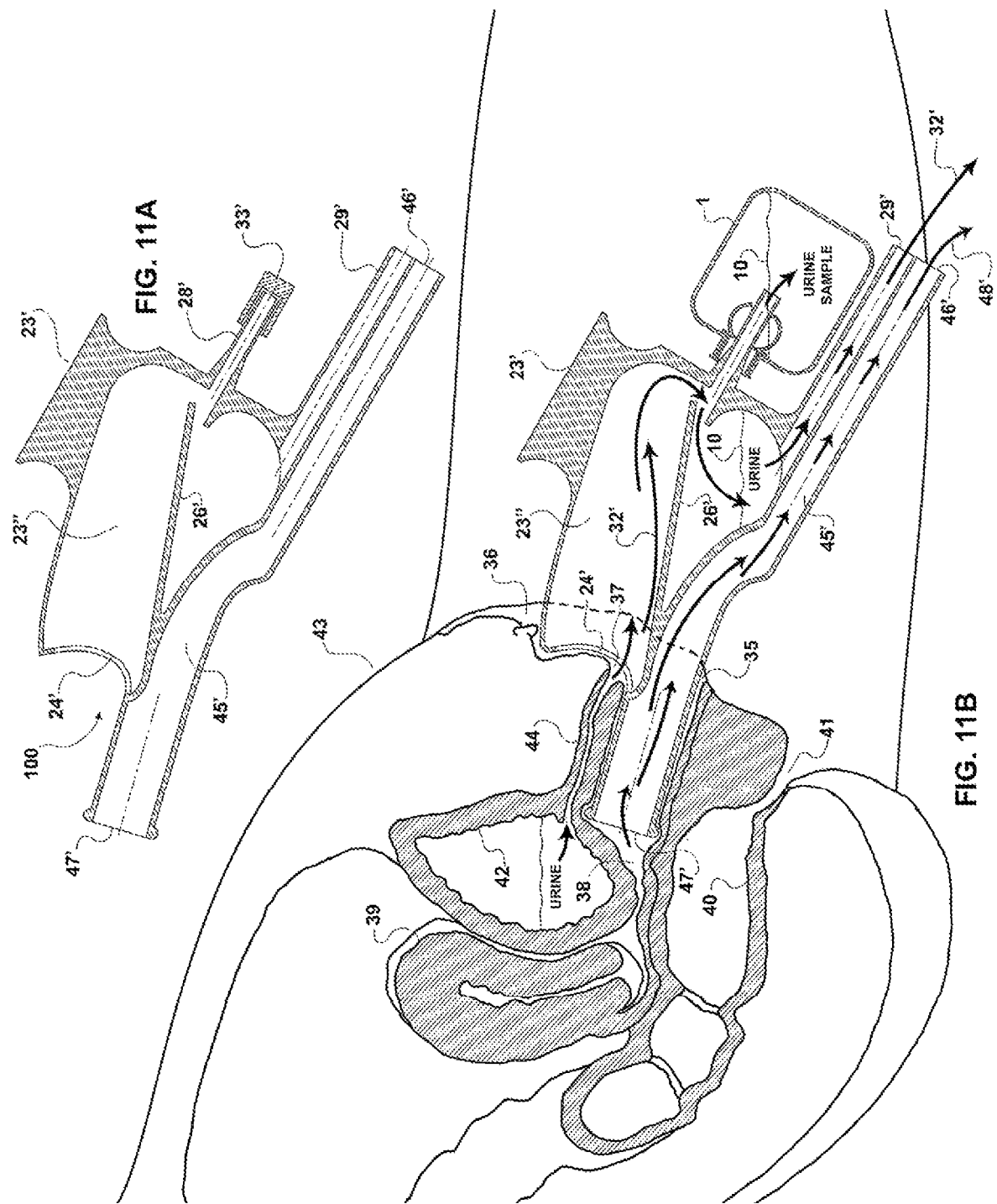

URINE-SPECIMEN COLLECTION, STORAGE, AND TESTING DEVICE

CROSS-REFERENCE TO RELATED APPLICATIONS

This application is a divisional of U.S. Non-provisional application Ser. No. 15/644,296, filed Jul. 7, 2017, (now U.S. Pat. No. 10,582,913), which is a continuation-in-part of U.S. Non-provisional application Ser. No. 14/557,791, filed Dec. 2, 2014, which claims priority from and the benefit of U.S. Provisional Application No. 61/963,459 filed Dec. 5, 2013, the disclosures of which are incorporated herein by reference in their entireties.

BACKGROUND

1. Field

The disclosed embodiment relates to the collection of a human urine-specimen, the storage of said urine-specimen and the primary testing or analysis of said urine-specimen.

2. Brief Description of Related Developments

The vast majority of existing urine specimen collection devices has one primary component in common and that is the generic plastic specimen-cup with a screw-on lid that is used in virtually every medical facility around the world.

Such specimen cups have one primary advantage, that being cheapness as related to manufacturing cost, which is important as billions of such specimen-cups are globally used each year and are intended to be disposable after only one use. Unfortunately, such traditional urine specimen-cups have a number of significant disadvantages.

The following is a list of disadvantages of existing traditional specimen-cups, not given in any order of significance:

Difficulty of implementation by a patient, especially female patients. It is difficult enough for a male patient to urinate into a specimen-cup without spillage or contamination of the exterior of the cup or of his own hand for that matter; however, it is virtually impossible for a female patient to urinate into such a specimen-cup without spillage or hand contamination primarily because of the nature of the female anatomy.

Also, a specimen-cup having a screw-on cap or lid which must be removed before use and then replaced after use may be difficult for many elderly or infirm patients to handle, some patients possibly having severe arthritis or other hand impairments. Potential spillage of the collected urine-sample becomes an issue in such circumstances.

Specimen contamination by the patient. Because the specimen-cup has a screw-on lid, this cover must first be unscrewed by the patient, the cup must be filled, and then the lid must be re-screwed onto the specimen-cup. All this physical handling of the specimen-cup by the patient significantly increases the possibility of contamination of the urine-specimen cup and lid, potentially rendering the urine-specimen useless through giving a false-analysis or a false diagnosis. Such a false-analysis requires a subsequent urine sample being taken thereby significantly increasing the total cost of the whole procedure.

Specimen contamination or spillage of the urine-specimen by the medical staff. Even if the medical staff is wearing protective gloves, handling a specimen-cup covered by urine on the exterior may lead to potential specimen contamination as the staff member un-screws the specimen-cup lid from the specimen-cup. Un-screwing and re-screwing the lid after a test-strip has been dipped into the urine-specimen increases the odds of specimen spillage therefore potential contamination of the work-space and other patient's specimen-cups or test-strips waiting to be read that may be stored in the same vicinity. It is common practice to read a number of different patients' specimens in succession in the same location as a simple matter of efficiency.

During normal clinic procedure, after the specimen-cup is uncovered, a urine-test-strip is manually dipped into the now exposed urine-specimen and the now urine-soaked test-strip is laid aside for a prescribed amount of time before said test-strip is "read" or compared to a control strip for primary analysis.

The problem here arises in that the urine-soaked test-strip may contaminate other patients' test-strips, contaminate the work-surface and most importantly, is now physically separated from the patients' specimen-container which carries the patients ID information. The potential miss-matching of test-strips and specimen-cups now becomes a very serious potential issue.

There exist a number of relatively expensive urine-specimen containers with self-contained test-strips. Except for the self-contained test-strip which requires almost immediate reading of the results, these devices still have a traditional screw or snap-on lid which must be dealt with the same as any other generic urine-specimen-cup and therefore have all the same numerous potential drawbacks previously mentioned.

There currently exits a urine-specimen container system known as the "BD VACUTAINER™". The lid to the specimen-cup in this system includes a semi-exposed hypodermic needle and prominent warning labels referring to the danger of said needle to both patient and medical staff.

The aspects of the disclosed embodiment are designed to address all the foregoing drawbacks and issues relative to prior art in an efficient and cost effective manner.

BRIEF DESCRIPTION OF THE DRAWINGS

The foregoing aspects and other features of the disclosed embodiment are explained in the following description, taken in connection with the accompanying drawings, wherein:

FIG. 1A is a cross-sectional side-view of the urine-specimen-container in accordance with aspects of the disclosed embodiment;

FIG. 1B is a cross-sectional side-view of a check valve of the urine specimen container of FIG. 1A in accordance with aspects of the disclosed embodiment;

FIG. 1C is a bottom exterior view of the check valve of FIG. 1B in accordance with aspects of the disclosed embodiment;

FIG. 1D is a cross-sectional side-view of the urine specimen container and the check valve of FIGS. 1A-1C in accordance with aspects of the disclosed embodiment;

FIG. 1E illustrates the urine specimen container of FIG. 1A co-operating with a tubular object in accordance with aspects of the disclosed embodiment;

FIG. 1F is a cross-sectional bottom view of the urine specimen container of FIG. 1A in accordance with aspects of the disclosed embodiment;

FIG. 1G is a cross-sectional bottom view of the urine specimen container of FIG. 1A in accordance with aspects of the disclosed embodiment;

FIG. 2A illustrates a urine collection attachment in accordance with aspects of the disclosed embodiment;

FIG. 2B is a cross-sectional side view of the urine collection attachment of FIG. 2A in accordance with aspects of the disclosed embodiment;

FIG. 2C illustrates the urine collection attachment of FIG. 2A properly attached to the urine specimen container of FIG. 1A in accordance with aspects of the disclosed embodiment;

FIG. 2D illustrates a urine stream flowing into the urine collection attachment and into the urine specimen container in accordance with aspects of the disclosed embodiment;

FIG. 2E illustrates a portion of a urine collection process in accordance with aspects of the disclosed embodiment;

FIG. 3A illustrates components of a urine test strip container assembly in accordance with aspects of the disclosed embodiment;

FIG. 3B is a schematic illustration of the urine test strip container assembly of FIG. 3A in accordance with aspects of the disclosed embodiment;

FIGS. 3C-3E illustrate the urine test strip container of FIG. 3A properly attached to the urine specimen container of FIG. 1A in accordance with aspects of the disclosed embodiment;

FIG. 4A illustrates a top and side cross-sectional view of a urine test panel container in accordance with aspects of the disclosed embodiment;

FIG. 4B illustrates the urine test panel container of FIG. 4A positioned just prior to being lowered into an access portion of the urine specimen container of FIG. 1A in accordance with aspects of the disclosed embodiment;

FIGS. 4C-4E illustrate the urine test panel container of FIG. 4A properly interfaced with the urine specimen container of FIG. 1A in accordance with aspects of the disclosed embodiment;

FIG. 5A illustrates a front cross-sectional view (AA), a side cross-sectional view and a rear view of a female-urinary-device (FUD) in accordance with aspects of the disclosed embodiment;

FIGS. 5B and 5C illustrate urine flow through the FUD into the urine specimen container of FIG. 1A in accordance with aspects of the disclosed embodiment;

FIG. 6A illustrates a cross-sectional side-view of the FUD of FIG. 5A in accordance with aspects of the disclosed embodiment;

FIG. 6B illustrates a cross-sectional side-view of a human pelvic region and a cross-sectional side-view of the FUD of FIG. 5A in accordance with aspects of the disclosed embodiment;

FIG. 7A illustrates a warning label found on a lid of BD VACUTAINER™ urine-specimen cups;

FIG. 7B illustrates a cross-sectional side-view of a BD VACUTAINER™ urine-specimen cup, a threaded screw-on lid and a top view of the lid;

FIGS. 7C-7E illustrate improvements of the BD VACUTAINER™ urine-specimen cup in accordance with aspects of the disclosed embodiment;

FIG. 10A illustrates a front cross-sectional view (AA), a side cross-sectional view and a rear view of an integrated menstrual and urine fluid interface in accordance with aspects of the disclosed embodiment;

FIGS. 10B and 10C illustrate urine flow through the integrated menstrual and urine fluid interface into the urine specimen container of FIG. 1A in accordance with aspects of the disclosed embodiment;

FIG. 11A illustrates a cross-sectional side-view of the integrated menstrual and urine fluid interface of FIG. 10A in accordance with aspects of the disclosed embodiment; and FIG. 11B illustrates a cross-sectional side-view of a human pelvic region and a cross-sectional side-view of the integrated menstrual and urine fluid interface of FIG. 10A in accordance with aspects of the disclosed embodiment.

DETAILED DESCRIPTION

Figure 8:
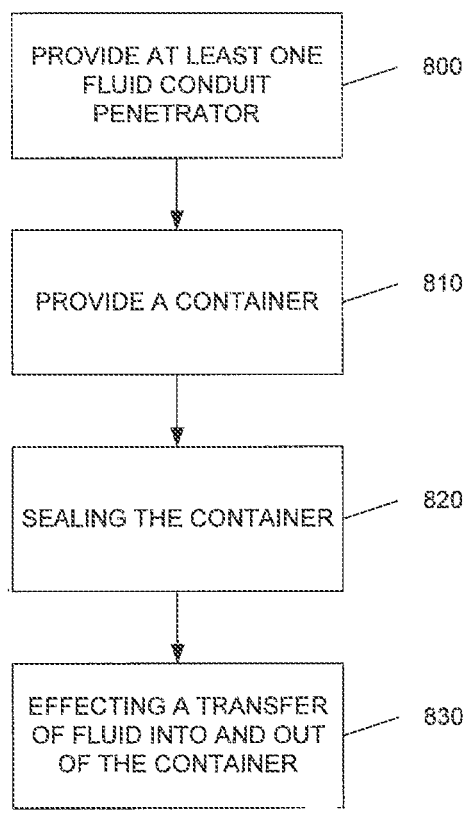
FIGS. 8 and 9 are flow diagrams in accordance with aspects of the disclosed embodiment.

The aspects of the disclosed embodiment overcome the disadvantages of the prior art in at least six significant ways (which are described in greater detail below):

First: the issue of potential contamination of the interior of said urine-specimen-container (also referred to as a urine-storage-container) (1) through physical contact by the patient or the medical staff is removed by the elimination of a need for a traditional screw-on lid through the implementation of an automatically self-closing check-valve device (3) regulating access to the interior of said urine-storage-container. A human hand or finger simply cannot physically pass through said check-valve and come into physical contact with the interior of said urine-specimen-container (1) or its contents.

Second: by virtue of the over-all design of said check-valve (3), accidental spillage of the contents of said urine-specimen-container (1) is also eliminated.

Third: through the implementation of a separate attachable urine-collection (6, 7, 12, 17, 23, 48) device designed to co-operate with said check-valve (3), said urine-specimen-container (1) is kept some distance away from the urine-stream during urine collection thereby significantly reducing the risk of urine coming into contact with either the urine-specimen-container's exterior or with the patient's hand holding the urine-specimen-container (1).

Fourth: through the implementation of a separate attachable urine test-strip-container device (12) designed to co-operate with said check-valve (3), any test-strips or reagents exposed to the urine specimen are at all times safely enclosed and isolated away from human contact within said test-strip container device (17).

Fifth: as the test-strips and reagents are at all times contained within said test-strip container device (17) and because the test-strip container (12) remains attached to the urine-specimen-container (1) until after the test-strip is analyzed, the potential issue of a test-strip being miss-matched to another patient's urine-specimen-container is eliminated.

Sixth: (The aforementioned BD VACUTAINER™ system includes a semi-exposed hypodermic needle attached to the lid of the specimen-cup container. Although there is a prominent warning label referring to this needle, medical staff commonly feels the need to warn patients of the danger of this needle while providing a urine-specimen. The aspects of the disclosed embodiment are designed to be able to co-operate with the BD VACUTAINER™ system is such a way as to limit potential exposure to the needle to trained medical staff only, thus making the system substantially safer for patients.

At no time during the whole process of urine-specimen collection through urine-specimen analysis is the urine-specimen exposed to human contact while properly implementing the aspects of the disclosed embodiment.

According to one aspect of the disclosed embodiment, a urine-specimen-container (1) includes a flat exterior bottom surface and an opposing upper access portal incorporating a check-valve device (3) having a normal closed condition.

Said check-valve (3) is designed to co-operate with any number of interchangeable system attachments (6, 7, 12, 17, 23, 48), that in one aspect may be considered a set, each of which can cause said check-valve to have an open condition when properly attached to said urine-specimen-container (1).

In a preferred aspect, said check-valve (3) has a one-piece construction design and is made of a flexible resilient synthetic material, that is, the material has an innate propensity to return to its original manufactured shape after being manually deformed or flexed. In a preferred aspect, said check-valve (3) may have a shape and form not dissimilar to a common infant's feeding bottle nipple; said nipple having a short slit (4) and (5) cleanly cut across the lower end of said nipple allowing for a small tubular object to pass through said slit.

According to another aspect of the disclosed embodiment, said urine-specimen-container (1) may co-operate with a temporarily attached urine-collection device having the sole function of facilitating the collection of urine from a flowing urine-stream. Said urine-collection device (7) may have a funnel shaped reservoir (8) at its top end and a hollow exit-tube (6) at its lower end; said hollow-tube (6) designed to co-operate with said check-valve (3) causing said check-valve (3) to have an open-condition when said hollow-tube (6) is manually passed through said check-valve (3). After a sufficient amount of urine has flowed into said urine-storage-container, said urine-collection device (7) is intended to be detached from said urine-specimen-container (1) and properly disposed of. Detaching said urine-collection device from said urine-storage-container causes said check-valve (3) to automatically resume its original closed condition thereby safely sealing the collected urine specimen within said urine-storage-container.

As the disposable urine-collection device (7) effectively separates the co-operating urine-storage-container by some distance from the urine-stream itself, both the exterior of said urine-storage-container and the patient's hand holding said urine-collection-container are substantially isolated from potential exposure to and contamination by the flowing urine-stream.

According to still another aspect of the disclosed embodiment, said urine-storage-container may co-operate with a temporarily attached urine test-strip-container device (12) having one function of isolating a generic urine test-strip from user contact both before and after said test-strip has been exposed to a urine-specimen and another function of keeping said test-strip physically related to the original urine-specimen-container thereby avoiding potential miss-matching of test-strip data to the wrong patient.

Said test-strip-container device (12) may be a simple transparent hollow-tube of sufficient internal diameter to accept a generic urine test-strip within said hollow-tube. Included is a separate slender rod or straw (14) with a means at one end of attaching a generic urine-test-strip; said straw (14) being able to move freely within said hollow-tube and being of a length preferably an inch or two longer then said hollow tube. In a preferred aspect, said straw (14) is indeed a simple common drinking straw of sufficient diameter to allow the non-reagent end of a generic test-strip to be securely lodged a short distance into one end of said straw. Of course, any other efficient means of securing the test-strip to the end of the straw may be employed.

Said test-strip-container device (12) may have an exterior flange (13) located close to its lower end regulating the depth said test-strip-container can be inserted into said urine-storage-container; said test-strip container device (12) is designed to co-operate with said check-valve (3) causing said check-valve (3) to have an open-condition when said test-strip container device (12) is manually passed through said check-valve (3).

With said test-strip-container device (12) properly attached to said urine-specimen-container, said combined rod or straw (14) and test-strip may be pushed downwards into said urine-specimen-container sufficient for the reagent-end of said test-strip to make full contact with the urine-sample collected within said urine-storage-container and immediately withdrawn up into said hollow tube only to a level where said test-strip is still contained within said transparent hollow-tube. After the prescribed waiting period for said generic test-strip, said test-strip may be safely viewed through said transparent hollow-tube and analyzed by comparison to a control-strip according to normal clinic procedure.

After said test-strip-container (12) has served its intended function, said device is intended to be detached from said urine-storage-container and properly disposed of. Detaching said test-strip-container device (12) from said urine-storage-container causes said check-valve to automatically resume its original closed condition thereby safely sealing the original collected urine specimen within said urine-storage-container ready for future testing or proper disposal.

Said test-strip, after making contact with the urine-sample has never been exposed to contact with the medical staff or any work surfaces and the original urine-sample remains at all times securely contained within said urine-storage-container safe from accidental spillage or unwanted contamination.

According to another aspect of the disclosed embodiment, said urine-storage-container may co-operate with an alternative temporarily attached test-strip or reagent container device (17); said alternative design intended to facilitate the testing of generic multi-panel urine test devices. Said alternative design being a hollow-tube designed to co-operate with said check-valve (3) causing said check-valve (3) to have an open condition when said hollow-tube (20) is passed through said check-valve (3). Said hollow tube may incorporate a transparent reservoir (18) at the top end of said hollow-tube (20), said reservoir sufficient in size and shape to contain one of a variety of commonly used generic multi-panel urine test devices. Said multi-panel test device container may also have a tapered exterior section (19) just below said reservoir designed to co-operate with said access portal (2) of said urine-storage-container forming an airtight seal between said tapered section (19) and said urine-specimen-container (1).

With said multi-panel test device container (17) properly attached to said urine-specimen-container (1) and a multi-panel test device (21) in place within said reservoir (18), said urine-specimen-container (1) may be manually squeezed sufficient to cause the urine sample contained within to flow upwards into said multi-panel container reservoir and just sufficient to temporarily make contact with the lower end of said generic multi-panel test device. Once the multi-panel test-device has been properly exposed to the urine sample, manual pressure is removed from the urine-storage-container thereby causing the urine sample to return to the interior of the urine-storage-container, leaving said urine-test-device container reservoir empty of urine.

After the prescribed waiting period, the multi-panel test device may be read through the transparent walls of said reservoir after which the test-device container device itself may be detached from the urine-storage-container, causing said check-valve to resume its normal closed condition. Said test-device and test device container may now be properly disposed of leaving the original urine-sample safely contained within said urine-storage-container for future testing or proper disposal.

According to another aspect of the disclosed embodiment, said urine-specimen-container (1) may co-operate with a temporally attached Female-Urinary-Device (23) commonly referred to as an FUD which is specifically designed to collect a urine sample from a female patient facilitating what is medically referred to as a "Clean-Catch" urine sample. A "Clean-Catch" urine-sample refers to a female urine-sample taken with the absolute minimum exposure of the urine-stream to outside contaminants potentially existing on the surfaces of the female vulva, labia or the vaginal opening.

Said FUD (23) being a hollow container comprising: 1) an entrance-portal (24) having a shape designed to accept urine-flow and also designed to surround and isolate the female urethral opening and therefore also the urine-stream from contact with anything other than the interior of said FUD device by forming a seal with the tissue immediately surrounding said urethral opening 2) a general exterior form conducive to comfortably fitting between the labia 3) a physical protruding shape (25) located immediately below said entrance-portal designed to fit snuggly into the vaginal opening thereby both sealing off the vagina and properly positioning said entrance-portal (24) over said urethral opening 4) an upper exit-tube (28) located opposite said entrance-portal (24) designed to co-operate with said urine-specimen-container (1) such that when passed through said check-valve (3), causes said check-valve (3) to have an open condition 5) a lower exit-tube/spillway (29) located just below the upper exit-tube (28) intended to drain any excess urine not collected within said urine-specimen-container (1) 6) an internal-shelf, baffle or partial partition (26) which substantially divides the interior or said FUD into an upper portion and a lower portion, said internal-shelf (26) designed to direct a majority of the urine-flow directly into said upper exit-tube (28) and therefore into said urine-specimen-container (1) but also positioned away from said upper exit-tube (28 sufficient to allow any excess urine to flow downwards into said lower interior portion and to exit said FUD via said lower exit-tube/spillway (29); said lower exit-tube (29) intended to co-operate with any commonly used urine storage bags or other collection device.

In an alternative non-medical aspect of said FUD, said upper exit-tube (28) and said internal shelf (26) could be excluded (or a cap (33) can be provided), allowing said FUD to function primarily as a method of facilitating female urination while the female is in a standing position, thereby affording any female all the advantages a male enjoys regarding the urination function. Due to the aforementioned features of said FUD, such a device would have significant hygienic advantages over any prior art for such a non-medical FUD device in that urine does not contact the labia, vulva or general pubic region as occurs in most prior art.

FIGS. 1A-1G illustrate both the urine-specimen-container and the check-valve device.

FIG. 1A is a cross-sectional side-view of the urine-specimen-container (1) showing the access-portal (2) which serves as access to the interior of said container (1). The urine-specimen-container (1) may be constructed of any suitable material commonly used for such urine-specimen-containers in the medical industry and may be of any size or shape having a flat bottom designed to keep the urine-specimen-container (1) in a stable upright position.

In one aspect the urine specimen container or fluid sample collection device includes at least one fluid conduit penetrator (6, 7, 12, 17, 23, 48) as described herein, and a container and penetration fitment (see e.g. the combination of container (1), check-valve (3) which includes slit (4, 5) with a valved opening penetration into the container, the valved opening penetration being configured to seal the container (1) and includes a valve, such as check-valve (3) configured to accept through the valve the at least one fluid conduit penetrator to effect a transfer of fluid into and out of the container (1). As described herein the at least one fluid conduit penetrator (6, 7, 12, 17, 23, 48) and the container and penetration fitment are configured for urine specimen collection. In one aspect the at least one fluid conduit penetrator (6, 7, 12, 17, 23, 48) is provided as a set of interchangeable fluid conduit penetrators.

FIG. 1B is a cross-sectional side-view of the check-valve (3) which permanently fits within portal (2) of urine-specimen-container (1). Check-valve (3) includes a slit at its lower end comprising two deformable opposing surfaces noted as surface (4) and surface (5). Surface (4) and surface (5) are shown contacting each other thereby indicating check-valve (3) is in its normal closed condition.

FIG. 1C is a bottom exterior view of the check-valve (3) showing a cleanly cut slit located in the bottom of check-valve (3). Said slit comprises two opposing surfaces (4) and (5) which are designed to have a normal condition such that when said opposing surfaces (4) and (5) meet, they form an effective barrier or seal against the movement of liquids through said check-valve (3).

Check-valve (3) may be constructed of any flexible synthetic material which reliably returns to its original shape and form after being manually deformed or flexed. In other words, the check-valve (3) is resiliently closable where the check-valve automatically opens from an insertion of the at least one fluid conduit penetrator (6, 7, 12, 17, 23, 48) through the check-valve (3). In one aspect, as described herein the check-valve (3) includes a resilient membrane having a slit (4) and (5) where the resilient membrane comprises a bulb having a convex surface extending into the container (1) where the slit (4) and (5) is located on the convex surface so as to be resilient to fluid pressure. The proven and preferred check-valve (3) design shown is very similar to a common infant's feeding-bottle nipple both in material and form with the addition of a slit (4) and (5) added to the end of the nipple. Of course, any other check-valve design with a normal closed condition could also function. An alternative functional design might comprise a flexible membrane with a centrally located pin-sized piercing which could be manually forced to expand radially to cause an open condition which automatically returns to a closed condition when said manually applied force is removed.

FIG. 1D illustrates a cross-sectional side-view of both urine-specimen-container (1) and check-valve (3) with check-valve (3) properly positioned within access-portal (2) of said container (1). Opposing surfaces (4) and (5) of check-valve (3) are seen in contact with each other indicating check-valve (3) is in its normal closed-condition. Any fluid contents contained within urine-specimen-container (1) would thereby be sealed within urine specimen container (1) regardless of the physical position or rotational attitude of said container (1).

FIG. 1E illustrates the urine-specimen-container (1) co-operating with a tubular object or fluid conduit penetrator (6) which is sized to accept urine stream collection. As will be described herein, in one aspect the tubular object (6) is interchangeable from a group of different fluid conduit penetrators (6, 7, 12, 17, 23, 48) each of which is configured for penetration of and interfacing with the check-valve (3)

and each having different predetermined characteristics that include, as described herein a hollow tube, a circular funnel, a test panel container, a female urinary device and a collection tube interface. Object (6) is a hollow-tube which represents a sub-part common to each of several attachments designed to attach to and co-operate with said urine-specimen-container (1). Said attachments being designed to facilitate both the collection and the testing of a urine specimen sealed within said urine-specimen-container (1). Attachment sub-part (6) being a hollow-tube which, when inserted through check-valve (3), parts the opposing flexible surfaces (4) and (5) of check-valve (3) thereby allowing for the free movement of fluids through hollow-tube sub-part (6). Sub-part (6) may also represent the lower end of a common laboratory pipette which could be used to extract a sample of the urine from within the urine-specimen-container.

FIG. 1F is a cross-sectional bottom view of urine-specimen-container (1) showing the check-valve (3) with opposing surfaces (4) and (5) in contact with each other thereby indicating check-valve (3) is in a closed condition.

FIG. 1G is a cross-sectional bottom-view of urine-specimen-container (1) showing the check-valve (3) in an open condition caused by the insertion of attachment sub-part (6) which has forced opposing flexible surfaces (4) and (5) to separate and no longer have physical contact with each other. When sub-part (6) is removed, opposing surfaces (4) and (5) of check-valve (3) will automatically resume contact with each other thereby reforming the original liquid-tight seal.

FIGS. 2A-2E illustrate the sequential steps of collecting a urine sample into urine-specimen-container (1) through the implementation of a urine-collection device or attachment (7).

FIG. 2A shows the urine-collection device (7) comprising a circular funnel-like form with the top (8) cut at a bias and a hollow exit-tube (6) at the bottom.

FIG. 2B shows a cross-sectional side view of the urine-collection attachment (7) entering urine-specimen-container (1) through access-portal (2) just prior to co-operating with check-valve (3) which is still in its normal closed condition.

FIG. 2C shows urine-collection attachment (7) properly attached to urine-specimen-container (1). The urine-collection attachment's lower exit-tube (6) has passed through check-valve (3) causing said check-valve (3) to assume its temporary open condition.

FIG. 2D shows a urine-stream (9) flowing into urine-collection attachment (7); passing through exit-tube (6) and finally into urine-specimen-container (1).

FIG. 2E shows the final step in the urine collection process wherein the urine-collection attachment (7), having served its urine collection purpose, has been detached from urine-collection-container (1) and has been properly disposed of. Check-valve (3) has automatically returned to its normal closed condition, thereby safely and automatically sealing the urine sample within urine-collection-container (1). The urine-specimen-container (1) is now ready to be handed over to the medical staff for analysis.

Urine-collection attachment (7) may be constructed of any material which will not contaminate the urine sample. There may be multiple alternative external shapes given to the urine-collection attachment (7) to be determined by such possible factors as the patient's gender, physical size, health condition or possibly even whether the patient is standing or reclining while the urine-specimen is being collected; all the while maintaining the primary function of collecting urine from a flowing urine-stream and simultaneously transferring the urine into said urine-specimen-container.

FIGS. 3A-3E illustrate the sequential steps of testing a urine-sample (10) contained with urine-specimen-container (1) utilizing urine-test-strip container assembly (A) designed to co-operate with said urine-specimen-container (1).

FIG. 3A shows the separate components of the urine test-strip-container assembly (A) comprising: a transparent hollow-tube (12); a rod (14) designed to move freely within said hollow-tube (12) and having a method of attaching a generic urine test-strip (15) to one end of said rod (14); rod (14) preferably being an inch or two longer in length than transparent hollow-tube (12). The bold arrow indicates rod (14) with attached test-strip (15) being inserted into the top end of transparent hollow-tube (12). A flange (13) at the lower end of hollow tube (12) regulates the proper depth to which hollow-tube (12) may be inserted into urine specimen-container (1).

FIG. 3B shows the urine test-strip-container assembly (A) positioned just prior to being inserted into urine-specimen container (7) which has a urine sample (10) ready to be analyzed. Check-valve (3) is seen in FIG. 2 in its normal closed and sealed condition.

FIG. 3C shows the assembled urine test-strip-container assembly (A) properly attached to urine-specimen-container (1) and co-operating with check-valve (3) now seen in its temporary open condition.

FIG. 3D shows the rod (14) having been manually pushed downwards into transparent hollow-tube (12) causing the reagent-end (16) of test-strip (15) to momentarily dip below the surface of the urine-sample (10).

FIG. 3E shows rod (14) and attached test-strip (15) being drawn upwards within transparent hollow-tube (12) to a position similar to that seen in FIG. 5 wherein the test strip is clearly visible but still contained within transparent hollow-tube (12). After the prescribed waiting period for the specific type of test-strip, the color of the reagent-end (16) of the urine-test strip (15) may be visually compared to a control-strip (11) for proper primary analysis of the urine sample.

The final step of the total procedure is the detachment and sanitary disposal of the urine test-strip-container assembly (A) leaving the original urine sample (10) safely and securely sealed within the urine-specimen-container (1) as it is seen back in FIG.-C2. Urine-specimen-container (1) may now be stored for future testing or be properly disposed of.

At no time from the point of urine collection to final disposal of all components of the disclosed embodiment has the urine sample been exposed to contact by either the patient or the medical staff involved in the procedure.

FIGS. 4A-4E illustrate the sequential steps of analyzing a urine-sample contained within urine-specimen-container (1) utilizing a urine test-panel-container (17) designed to attach to and co-operate with said urine-specimen-container (1).

FIG. 4A shows top and side cross-sectional views of said urine-test-panel-container (17) Said test-panel-container comprises a transparent upper rectangular reservoir (18) with a lower exit-tube (20) having an upper tapered section (19).

FIG. 4B shows urine test-panel-container (17) positioned just prior to being lowered into access-portal (2) of urine-specimen-container (1) containing a previously collected urine specimen (10). Check-valve (3) is in its normal closed and sealed condition.

FIG. 4C shows test-panel-container (17) properly attached to urine-specimen-container (1) having caused check-valve (3) to assume an open condition. The tapered section (19) of exit-tube (20) is and must be seated firmly within urine-specimen-container entrance-portal (2) forming an air-tight seal. Also shown is a generic four-panel urine-test-panel (21) being lowered into reservoir (18).

FIG. 4D shows urine-specimen-container (1) being manually compressed at points (P-P) thereby forcing the collected urine-specimen (10) to flow upwards into reservoir (18) of test-panel-container (17) sufficient to cover the lower end of urine-test-panel (21).

FIG. 4E shows urine-specimen-container (1) in its normal uncompressed condition after the external pressure has been removed thereby allowing urine in reservoir (18) to drain back down into urine-specimen-container (1). After a designated waiting period, the analyzed results for urine-test-panel (21) may be read through the transparent sides of test-panel-container (17).

The final step of the total procedure being the detachment and sanitary disposal of the urine test-panel-container (17) leaving the original urine sample safely and securely sealed within the urine-specimen-container (1) with check-valve (3) having automatically returned to its normal closed and sealed condition. Urine-specimen-container (1) may now be stored for future testing or properly disposed of.

At no time from the point of urine collection to final disposal of all the used components of the disclosed embodiment have the urine-sample or the activated urine test-panel been exposed to contact by either the patient or the medical staff involved in the procedure.

FIGS. 5A-5C illustrate a urine-collecting attachment (23) specific to the female gender and commonly referred to as a FUD or Female-Urinary-Device. As will be described herein, in one aspect, the female urinary device includes a collection container having a discharge opening or exit tube (28) and a collection opening or entrance portal (24), the collection opening (24) being configured to surround and isolate a urethral opening; an internal baffle or shelf (26) that cooperates with at least a urine sample container (1) to provide a spillway or overflow (leading to exit tube 29) to the discharge opening (28), where the spillway provides urine passage to a collection tank or otherwise provides passage from the collection container to any suitable location. As will also be described herein the FUD includes a probe or vaginal insert protrusion (25) configured for interior engagement with a vaginal opening for placement of the collection opening (24) relative to the urethral opening. As will be described herein, in one aspect, the internal baffle (26) is disposed within the FUD collection container. In one aspect, as will be described herein, the discharge opening (28) includes or otherwise forms a fluid conduit penetrator configured for insertion into the urine sample container (1). In one aspect, the FUD includes a cap (33) configured to engage and close off the fluid conduit penetrator or discharge opening (28) to effect a flow of urine directly out of the spillway or exit tube (29).

FIG. 5A has a front cross-sectional view (AA); a side cross-sectional view and a rear view of said FUD-attachment (23). FUD-attachment (23) is specifically designed to facilitate the collection of a female urine-specimen with the least possible chance of contamination from potential contaminants commonly found on the surfaces of the vulva, the labia or within the vagina. How this FUD-attachment (23) physically co-operates with the female anatomy is fully illustrated Drawing-F.

FUD-attachment (23) is basically a hollow container comprising: an entrance portal (24); two exit-tubes (28) and (29); a vaginal insert protrusion (25); an upper-internal shelf (26); a lower-internal shelf (27) and two gripping points (30) and (31). Exit-tube (28) is designed to co-operate with urine-specimen-container (1).

Vaginal insert protrusion (25) facilitates the proper positioning of entrance-portal (24) over the urethral-opening and between the labia and also effectively seals or plugs the vaginal-opening. The edges or boundaries of entrance-portal (24) are shaped to surround the female urethral-opening forming a tight seal against contamination potentially found on tissues located outside the boundaries of said entrance-portal (24).

Gripping points (30) and (31) are intended to be used by the patient to hold said FUD-attachment firmly in position while urination occurs.

FIG. 5B shows the direction of the urine flow (32) through entrance-portal (24), over and along upper-shelf (26), down to lower-shelf (27), into upper exit-tube (28) and finally into urine-specimen-container (1). Exit-tube (28) has caused check-valve (3) to have an open condition.

FIG. 5C shows the collected urine having risen to a level (10) which covers exit-tube (28). At this level, no further urine can enter the urine-specimen-container (1) thus forcing any further urine to back-up and flow underneath upper-shelf (26), over the edge of lower-shelf (27) and to exit the FUD-attachment (23) via lower exit-tube (29). Depending on the circumstances during urine-specimen collection, this urine overflow could be directed into a toilet, a urine collection bag or any other desired container.

Once the patient's bladder is empty, the FUD-attachment (23) may be detached from contact with the patient and after the FUD-attachment (23) is detached from the urine-specimen-container (1), it may be properly disposed of. The FUD-attachment (23) is intended to be an inexpensive disposable item intended for one-time use only.

FIGS. 6A-6B illustrate a urine-collecting attachment specific to the female gender and commonly referred to as a FUD or Female-Urinary-Device. This drawing illustrates the FUD-attachment (23) properly positioned relative to the human female anatomy (43) in order to facilitate an un-contaminated urine-specimen collection.

FIG. 6A shows a cross-sectional side-view of said FUD-attachment (23). FUD-attachment (23) is specifically designed to facilitate the collection of a female urine specimen with the least possible chance of contamination from potential contaminants commonly found on the surfaces of the vulva, the labia or within the vagina. FUD-attachment (23) is basically a hollow container comprising: an entrance portal (24); two exit-tubes (28) and (29); a vaginal insert protrusion (25) and an internal shelf (26). Exit-tube (28) is designed to co-operate with the check-valve (3) of urine-specimen-container (1).

Vaginal insert protrusion (25) facilitates the proper positioning of entrance-portal (24) over the urethral-opening and between the labia and also plugs the vaginal-opening. The edges of entrance-portal (24) physically surround the urethral-opening forming a seal against contamination from tissues outside the boundaries of said entrance-portal (24).

A cap (33) intended to close off exit-tube (28) would be used at times a urine specimen was not being collected thereby causing the urine to flow directly out of exit-tube (29). With exit-tube (28) closed off or as in one possible aspect, not existing at all, the FUD (23) could serve to allow a female to urinate while in a standing position with all the advantages that the male gender enjoys. In such an aspect, shelf (26) would also not be necessary.

FIG. 6B shows a cross-sectional side-view of the human female pelvic region (43) and a cross-sectional side-view of said FUD-attachment (23) attached to urine-specimen-container (1).

The female pelvic region diagram (43) shows the uterus (39); the rectum (40); the anus (41); the bladder (42); the vagina (38); the vaginal opening (35) the labia (11); the urethra (44) and the urethral opening (37).

The FUD-attachment (23) is shown properly positioned with the vaginal-protrusion (25) inserted into the vagina (38). The entrance portal (24) into the FUD-attachment (23) is shown covering the urethral opening (37) and the FUD-attachment (23) is shown located between the labia (36).

The bold directional arrows (32) indicate the urine-stream exiting the bladder (42) via the urethral opening (37), flowing over and along self (26) and into urine-specimen-container (1) which is shown filled to a level (10) causing the remaining urine flow (32) to be redirected under shelf (26) to a lower FUD (23) chamber where it exits out of exit-tube (29).

Exit-tube (29) may connect to a urine collection bag and any other urine collection device intended for urine-output measurement and disposal. All mechanical components show in this drawing are intended for one-time use only.

FIGS. 7A-7E illustrate an aspect of the disclosed embodiment wherein the commonly used BD-VACUTAINER™ system may be modified to co-operate with the aspects of the disclosed embodiment thereby overcoming some significant inherent negative issues existing in the BD VACUTAINER™ system as it currently exits.

FIG. 7A represents the warning-label (48) found on the lid (45) of BD VACUTAINER™ conventional urine-specimen cups.

FIG. 7B includes a cross-sectional side-view of a BD VACUTAINER™ conventional urine-specimen-cup (51), a threaded (50) screw-on lid (45) and also a top-view of said lid (45). Specimen-cup (51) is a normal generic style urine-specimen-cup.

Screw-on lid (45) differs from other generic lids in that it includes a protrusion projecting from its underside comprising: a cylindrical reservoir (47) housing a centrally located hypodermic needle (46) projecting upwards from the base of said reservoir (47) and a centrally located hollow-tube (48) projecting downwards from the base of reservoir (47). Warning label (48) is shown properly positioned over reservoir (47).

Said BD VACUTAINER™ conventional specimen-cup (51) has all the disadvantages associated with such generic specimen-cups which have already been thoroughly discussed.

The obvious disadvantage of the BD VACUTAINER™ lid (45) design is the inclusion of a hypodermic needle which requires the warning-label (48) and in most cases, also an additional verbal warning to patients by medical staff.

FIGS. 7C, 7D and 7E illustrate improvements to the BD VACUTAINER™ conventional urine collection system as related to the aspects of the disclosed embodiment. One significant improvement from elimination of the container screw on cap results in the patients not being exposed to the hypodermic needle; only the medical-staff are exposed to the hypodermic needle (46) in the aspects of the disclosed embodiment. A second significant improvement is the implementation the urine-storage-container (1) with all its attending advantages as previously described.

FIG. 7C illustrates a cross-sectional side-view and also a top-view of component (A) which is substantially the same as lid (45) as seen in FIG.-G2 minus everything except for the reservoir (47), the hypodermic-needle (46) and the hollow-tube (48).

FIG. 7D illustrates urine-storage-container (1) of the aspects of the disclosed embodiment as the patient would experience it; that is, no hypodermic-needle.

FIG. 7E illustrates a BD VACUTAINER™ conventional urine-collection tube about to co-operate with components (A) and (1) of the aspects of the disclosed embodiment. Only the trained medical staff is involved during this step of the procedure.

BD VACUTAINER™ conventional collection-tube (52) is a hollow transparent small test-tube device sealed by plug (53). The collection-tube (52) contains a near vacuum or negative-pressure at this stage of use.

When BD VACUTAINER™ conventional tube is pressed downwards into reservoir (47); hypodermic-needle (46) pierces plug (52). The negative pressure within tube (52) causes the urine within urine-storage-container (1) to be sucked up into tube (52) through hollow-tube (48) and through hypodermic needle (46). The filled BD VACUTAINER™ tube may now be removed for transport to another facility or laboratory for analysis.

In one aspect a method of fluid sample collection includes providing at least one fluid conduit penetrator (6, 7, 12, 17, 23, 48) (FIG. 8, Block 800), providing a container (1) (FIG. 8, Block 810) and sealing the container with a valved opening penetration of a penetration fitment (FIG. 8, Block 820), where the valved opening penetration includes a valve, such as check-valve (3) configured to accept through the valve the at least one fluid conduit penetrator for effecting a transfer of fluid into and out of the container (1) (FIG. 8, Block 830). In one aspect the method includes automatically opening the valve from an insertion of the at least one fluid conduit penetrator through the valve. In one aspect the method includes resiliently closing the valve from a removal of the at least one fluid conduit penetrator from the valve. As described herein, in one aspect, the at least one fluid conduit penetrator is sized to accept urine stream collection.

Figure 9:
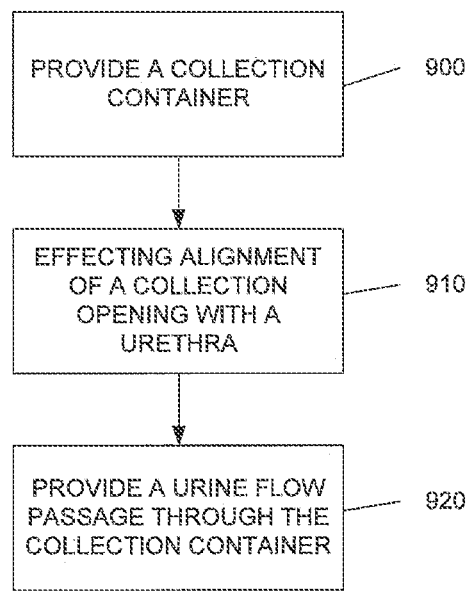

In one aspect a method of discharging urine with the female urinary device attachment (23) includes providing a collection container having a discharge opening and a collection opening (FIG. 9, Block 900), the collection opening being configured to surround and isolate a urethral opening; effecting alignment of a collection opening of the female urinary device with a urethra with a probe of the female urinary device (FIG. 9, Block 910), where the probe is configured for insertion into a vaginal opening; and providing a urine flow passage through the collection container to effect discharge of urine from the collection container through one or more of the discharge opening (28) and the spillway (e.g. through exit tube 29) (FIG. 9, Block 920). In one aspect the method includes providing the internal baffle (26) within the collection container that cooperates with at least urine sample container (1) (and in other aspects the cap 33) to provide the spillway to the discharge opening (28) which provides urine passage out of the collection container. In one aspect the method includes providing the cap (33) that engages with and closes off the discharge opening (289) effecting a flow of urine through the spillway and out of the collection container. In one aspect the alignment of the collection opening (24) of the female urinary device with the urethra occurs with the female standing or sitting in a reclined position, and discharge of urine from the collection container occurs with the female standing or sitting in the reclined position.

FIGS. 10A-10C illustrate an integrated menstrual and urine fluid interface device (23'). In one aspect, the integrated menstrual and urine fluid interface device (23') is generally similar to the female urinary device (23) described previously (similar features having similar reference numbers). The integrated menstrual and urine fluid interface device (23') includes a urine stream collection chamber 23" having a urine discharge opening (28') and a urine stream collection opening (24'), the urine stream collection opening (24') being configured to surround and isolate a urethral opening; an internal baffle (26') that cooperates with at least the urine sample container (1) to direct urine to the urine discharge opening (28') and to provide a spillway or overflow (leading to exit tube 29'), where the spillway provides urine passage to a urine collection bag, any other urine collection device or otherwise provides passage from the collection container to any suitable location. In one aspect, the integrated menstrual and urine fluid interface device (23') also includes a cap (33'), a lower-internal shelf (27'), and two gripping points (30') and (31').

In one aspect, the integrated menstrual and urine fluid interface device (23') further includes a menstrual fluid passage (45'). The menstrual fluid passage (45') including a menstrual fluid discharge opening (46') and a menstrual fluid collection opening (47') In one aspect, the menstrual fluid collection opening (47') includes a neck (47N') and a lip (47L'). In one aspect, the menstrual fluid passage (45') is isolated from the urine stream collection chamber by, for example, a partition wall. In one aspect, at least a portion of the menstrual fluid passage (45') is defined by an edge of the urine stream collection opening forming an integrated interface (100) of the integrated menstrual and urine fluid interface device (23'). In one aspect, the integrated menstrual and urine fluid interface device (23') is configured, via the integrated interface (100) including the neck (47N') of the menstrual fluid collection opening (47') and the edge of the urine stream collection opening (24'), for engagement with a vaginal opening to provide menstrual fluid passage from the menstrual fluid passage (45') to any suitable location, for example, substantially similar to collection of urine described previously. In one aspect, the integrated menstrual and urine fluid interface device (23') is inserted into the vaginal opening which effects engagement with the interior of the vaginal opening and coincidentally places the urine stream collection opening (24') relative to the urethral opening.

FIG. 10A has a front cross-sectional view (AA'); a side cross-sectional view and a rear view of said integrated menstrual and urine fluid interface device (23'). The integrated menstrual and urine fluid interface device (23') is specifically designed to facilitate the collection of a female urine-specimen with the least possible chance (substantial elimination of risk) of contamination from potential contaminants commonly found on the surfaces of the vulva, the labia or within the vagina, while also providing disposal of menstrual fluids, preventing the menstrual fluids from contaminating the urine sample. Insertion of the menstrual fluid collection opening (47') effects engagement of the integrated interface (100) with the vaginal opening and the urethral opening such that menstrual fluid is captured by the menstrual fluid passage (45') and the neck (47N') of the menstrual fluid collection opening (47') drawing the menstrual fluid away from the urine stream collection opening (24').

The integrated menstrual and urine fluid interface device (23') facilitates the proper positioning, such that the menstrual fluid collection opening (47') is inserted into the vaginal opening coincident with the urine stream collection opening (24') being placed over the urethral-opening and between the labia effectively preventing contaminants from contaminating the urine or the (23") and also effectively provides passage of menstrual fluid away from the urethral-opening, as described previously, to, for example, a urine collection bag to prevent contamination of a urine sample.

FIG. 10B is substantially similar to FIG. 5B, illustrating the direction of the urine flow (32'), while also illustrating the direction of menstrual fluid flow (48') through the menstrual fluid passage (45').

FIG. 10C is substantially similar to FIG. 5C illustrating the collected urine having risen to a level (10) which covers exit-tube (28'), while also illustrating menstrual fluid flow (48') through the menstrual fluid passage (45').

Once the patient's bladder is empty, integrated menstrual and urine fluid interface device (23') may be detached from contact with the patient, (i.e., the interface device (23') is removed from the vaginal opening) and after the integrated menstrual and urine fluid interface device (23') is detached from the urine-specimen-container (1), it may be properly disposed of. The integrated menstrual and urine fluid interface device (23') is intended to be an inexpensive disposable item intended for one-time use only.

FIGS. 11A-11B illustrate the integrated menstrual and urine fluid interface device (23') properly positioned relative to the human female anatomy (43) in order to facilitate an un-contaminated urine-specimen collection, including proper disposal of menstrual fluid.

FIG. 11A shows a cross-sectional side-view of said integrated menstrual and urine fluid interface device (23'), substantially similar to the FUD-attachment (23) illustrated in FIG. 6A, however further including menstrual fluid passage (45') for collection of menstrual fluid for the least possible chance of contamination the urine-specimen.

FIG. 11B shows a cross-sectional side-view of the human female pelvic region (43) and a cross-sectional side-view of said integrated menstrual and urine fluid interface device (23'), substantially similar to the FUD-attachment (23) illustrated in FIG. 6A, attached to urine-specimen-container (1).

In accordance with one or more aspects of the disclosed embodiment a urine-specimen collection, storage and testing device or system includes a urine-specimen-container including a hollow-interior and an access-portal incorporating a self-closing check-valve component which regulates all access to said hollow-interior; attachable urine-collection components and attachable urine-testing components each designed to co-operate with said self-closing check-valve component such that a collected urine-specimen and any catalytic or other reagents and testing substances are at all times kept isolated from human contact during the whole process of urine-specimen collection, urine-specimen storage and urine-specimen testing.

In accordance with one or more aspects of the disclosed embodiment a fluid sample collection device includes at least one fluid conduit penetrator; and a container and penetration fitment with a valved opening penetration into the container, the valved opening penetration being configured to seal the container and includes a valve configured to accept through the valve the at least one fluid conduit penetrator to effect a transfer of fluid into and out of the container.

In accordance with one or more aspects of the disclosed embodiment the at least one fluid conduit penetrator and the container and penetration fitment are configured for urine specimen collection.

In accordance with one or more aspects of the disclosed embodiment the valve is resiliently closable.

In accordance with one or more aspects of the disclosed embodiment the valve automatically opens from an insertion of the at least one fluid conduit penetrator through the valve.

In accordance with one or more aspects of the disclosed embodiment the at least one fluid conduit penetrator is sized to accept urine stream collection.

In accordance with one or more aspects of the disclosed embodiment the valve comprises a resilient membrane having a slit.

In accordance with one or more aspects of the disclosed embodiment the resilient membrane comprises a bulb having a convex surface extending into the container where the slit is located on the convex surface so as to be resilient to fluid pressure.

In accordance with one or more aspects of the disclosed embodiment the at least one fluid conduit penetrator is interchangeable from a group of different fluid conduit penetrators each of which is configured for penetration of and interfacing with the valve and each having different predetermined characteristics.

In accordance with one or more aspects of the disclosed embodiment the different predetermined characteristics comprise a hollow tube, a circular funnel, a test panel container, a female urinary device and a collection tube interface.

In accordance with one or more aspects of the disclosed embodiment a urine sample collection device includes a set of interchangeable fluid conduit penetrators; and a container and penetration fitment with a valved opening penetration into the container, the valved opening penetration being configured to seal the container and includes a valve configured to accept through the valve each fluid conduit penetrator of the set of interchangeable fluid conduit penetrators to effect a transfer of fluid into and out of the container.

In accordance with one or more aspects of the disclosed embodiment the set of interchangeable fluid conduit penetrators and the container and penetration fitment are configured for urine specimen collection.

In accordance with one or more aspects of the disclosed embodiment the valve is resiliently closable and automatically opens from an insertion of the at least one fluid conduit penetrator through the valve.

In accordance with one or more aspects of the disclosed embodiment the valve comprises a resilient membrane having a slit.

In accordance with one or more aspects of the disclosed embodiment the resilient membrane comprises a bulb having a convex surface extending into the container where the slit is located on the convex surface so as to be resilient to fluid pressure.

In accordance with one or more aspects of the disclosed embodiment each fluid conduit penetrator of the set of interchangeable fluid conduit penetrators has a different predetermined characteristic from other ones of the fluid conduit penetrators in the set of interchangeable fluid conduit penetrators, the different predetermined characteristics comprising a hollow tube, a circular funnel, a test panel container, a female urinary device and a collection tube interface.

In accordance with one or more aspects of the disclosed embodiment a method of fluid sample collection includes providing at least one fluid conduit penetrator; providing a container; sealing the container with a valved opening penetration of a penetration fitment, where the valved opening penetration includes a valve configured to accept through the valve the at least one fluid conduit penetrator for effecting a transfer of fluid into and out of the container.

In accordance with one or more aspects of the disclosed embodiment the method further includes automatically opening the valve from an insertion of the at least one fluid conduit penetrator through the valve.

In accordance with one or more aspects of the disclosed embodiment the method further includes resiliently closing the valve from a removal of the at least one fluid conduit penetrator from the valve.

In accordance with one or more aspects of the disclosed embodiment the at least one fluid conduit penetrator is sized to accept urine stream collection.

In accordance with one or more aspects of the disclosed embodiment the at least one fluid conduit penetrator is interchangeably provided from a group of different fluid conduit penetrators each of which is configured for penetration of and interfacing with the valve and each having different predetermined characteristics, where the different predetermined characteristics comprising a hollow tube, a circular funnel, a test panel container, a female urinary device and a collection tube interface.

In accordance with one or more aspects of the disclosed embodiment a method of fluid sample collection includes providing at least one fluid conduit penetrator; providing a container; and sealing the container with a valved opening penetration of a penetration fitment, where the valved opening penetration includes a valve configured to accept through the valve the at least one fluid conduit penetrator for effecting a transfer of fluid into and out of the container.

In accordance with one or more aspects of the disclosed embodiment the method further includes automatically opening the valve from an insertion of the at least one fluid conduit penetrator through the valve.

In accordance with one or more aspects of the disclosed embodiment the method further includes resiliently closing the valve from a removal of the at least one fluid conduit penetrator from the valve.

In accordance with one or more aspects of the disclosed embodiment the at least one fluid conduit penetrator is sized to accept urine stream collection.

In accordance with one or more aspects of the disclosed embodiment the at least one fluid conduit penetrator is interchangeably provided from a group of different fluid conduit penetrators each of which is configured for penetration of and interfacing with the valve and each having different predetermined characteristics, where the different predetermined characteristics comprising a hollow tube, a circular funnel, a test panel container, a female urinary device and a collection tube interface.

A female urinary device including a urine stream collection container having a discharge opening and a stream collection opening, the stream collection opening being configured to surround and isolate a urethral opening; an internal baffle that cooperates with at least a urine sample container to provide a spillway to the discharge opening, where the spillway provides urine passage to a collection tank; and a probe configured for interior engagement with a vaginal opening for placement of the stream collection opening relative to the urethra opening.

In accordance with one or more aspects of the disclosed embodiment the internal baffle is disposed within the urine stream collection container.

In accordance with one or more aspects of the disclosed embodiment the discharge opening includes a fluid conduit penetrator configured for insertion into the urine sample container.

In accordance with one or more aspects of the disclosed embodiment the female urinary device further includes a cap configured to engage and close off the fluid conduit penetrator to effect a flow of urine directly out of the spillway.

In accordance with one or more aspects of the disclosed embodiment a method of discharging urine with a female urinary device includes providing a urine stream collection container having a discharge opening and a stream collection opening, the stream collection opening being configured to surround and isolate a urethral opening; effecting alignment of the stream collection opening of the female urinary device with a urethra with a probe of the female urinary device, where the probe is configured for insertion into a vaginal opening; and providing a urine flow passage through the urine stream collection container to effect discharge of urine from the urine stream collection container through one or more of the discharge opening and a spillway.

In accordance with one or more aspects of the disclosed embodiment the method further includes providing an internal baffle within the urine stream collection container that cooperates with at least urine sample container to provide the spillway to the discharge opening which provides urine passage out of the urine stream collection container.

In accordance with one or more aspects of the disclosed embodiment the method further includes providing a cap that engages with and closes off the discharge opening effecting a flow of urine through the spillway and out of the urine stream collection container.

In accordance with one or more aspects of the disclosed embodiment the alignment of the collection opening of the female urinary device with the urethra occurs with the female standing or sitting in a reclined position, and discharge of urine from the collection container occurs with the female standing or sitting in the reclined position.

In accordance with one or more aspects of the disclosed embodiment an integrated menstrual and urine fluid interface device is provided. The integrated menstrual and urine fluid interface device including a urine stream collection chamber having a urine discharge opening and a urine stream collection opening, the urine stream collection opening having an edge being configured to surround and isolate a urethral opening, an internal baffle that cooperates with at least a urine sample container to provide a spillway to the urine discharge opening, where the spillway provides urine passage to a collection tank, and a menstrual fluid passage having a menstrual fluid discharge opening and a menstrual fluid collection opening, the menstrual fluid passage being isolated from the urine stream collection chamber, wherein at least a portion of the menstrual fluid passage is defined by the edge of the urine stream collection opening forming an integrated interface, the integrated interface configured for placement of the urine stream collection opening relative to the urethra opening and for interior engagement with a vaginal opening to provide substantially simultaneous passage through the menstrual fluid passage and urine stream collection chamber for passage of menstrual and urine fluid, respectively, to the collection tank.

In accordance with one or more aspects of the disclosed embodiment the internal baffle is disposed within the urine stream collection container.

In accordance with one or more aspects of the disclosed embodiment the urine discharge opening includes a fluid conduit penetrator configured for insertion into the urine sample container.

In accordance with one or more aspects of the disclosed embodiment a cap configured to engage and close off the fluid conduit penetrator to effect a flow of urine directly out of the spillway.

In accordance with one or more aspects of the disclosed embodiment a method of discharging urine and menstrual fluid with an integrated menstrual and urine fluid interface device. The method including providing a urine stream collection chamber having a urine discharge opening and a urine stream collection opening, the urine stream collection opening having an edge being configured to surround and isolate a urethral opening, providing a menstrual fluid passage having a menstrual fluid discharge opening and a menstrual fluid collection opening, the menstrual fluid passage being isolated from the urine stream collection chamber, wherein a portion of the menstrual fluid passage is defined by the edge of the urine stream collection opening forming an integrated interface configured for interior engagement with a vaginal opening, inserting the integrated interface into the vaginal opening, effecting alignment of the urine stream collection opening with a urethra, and providing substantially simultaneous passage through the menstrual fluid passage and urine stream collection chamber to effect discharge of the menstrual fluid from the menstrual fluid passage through the menstrual fluid discharge opening and discharge of urine from the urine stream collection chamber through one or more of the urine discharge opening and a spillway.

In accordance with one or more aspects of the disclosed embodiment the method further includes providing an internal baffle within the urine stream collection chamber that cooperates with at least urine sample container to provide the spillway to the discharge opening which provides urine passage out of the urine stream collection chamber.

In accordance with one or more aspects of the disclosed embodiment the method further includes providing a cap that engages with and closes off the discharge opening effecting a flow of urine through the spillway and out of the urine stream collection chamber.

In accordance with one or more aspects of the disclosed embodiment the alignment of the urine stream collection opening with the urethra occurs with the female standing or sitting in the reclined position, and discharge of urine from the urine stream collection chamber occurs with the female standing or sitting in the reclined position.

In accordance with one or more aspects of the disclosed embodiment the insertion of the integrated interface with the vaginal opening occurs with the female standing or sitting in a reclined position, and discharge of menstrual fluid from the menstrual fluid passage occurs with the female standing or sitting in the reclined position.

It should be understood that the foregoing description is only illustrative of the aspects of the disclosed embodiment. Various alternatives and modifications can be devised by those skilled in the art without departing from the aspects of the disclosed embodiment. Accordingly, the aspects of the disclosed embodiment are intended to embrace all such alternatives, modifications and variances that fall within the scope of the appended claims. Further, the mere fact that different features are recited in mutually different dependent or independent claims does not indicate that a combination of these features cannot be advantageously used, such a combination remaining within the scope of the aspects of the disclosed embodiment.

What is claimed is:

1. A female urinary device comprising
a urine stream collection container having a discharge opening and a stream collection opening, the stream collection opening being configured to surround and isolate a urethral opening;
an internal baffle that cooperates with at least a urine sample container to provide a spillway to the discharge opening, where the spillway provides urine passage to a collection tank; and
a probe configured for interior engagement with a vaginal opening for placement of the stream collection opening relative to the urethra opening.

2. The female urinary device of claim 1, wherein the internal baffle is disposed within the urine stream collection container.

3. The female urinary device of claim 1, wherein the discharge opening includes a fluid conduit penetrator configured for insertion into the urine sample container.

4. The female urinary device of claim 3, wherein the female urinary device further includes a cap configured to engage and close off the fluid conduit penetrator to effect a flow of urine directly out of the spillway.

5. A method of discharging urine with a female urinary device, the method comprising
providing a urine stream collection container having a discharge opening and a stream collection opening, the stream collection opening being configured to surround and isolate a urethral opening;
effecting alignment of the stream collection opening of the female urinary device with a urethra with a probe of the female urinary device, where the probe is configured for insertion into a vaginal opening; and
providing a urine flow passage through the urine stream collection container to effect discharge of urine from the urine stream collection container through one or more of the discharge opening and a spillway.

6. The method of claim 5, further comprising providing an internal baffle within the urine stream collection container that cooperates with at least a urine sample container to provide the spillway to the discharge opening which provides urine passage out of the urine stream collection container.

7. The method of claim 5, further comprising providing a cap that engages with and closes off the discharge opening effecting a flow of urine through the spillway and out of the urine stream collection container.

8. The method of claim 5, wherein the alignment of the stream collection opening of the female urinary device with the urethra occurs with the female standing or sitting in a reclined position, and discharge of urine from the urine stream collection container occurs with the female standing or sitting in the reclined position.

9. A method of discharging urine and menstrual fluid with an integrated menstrual and urine fluid interface device, the method comprising:
providing a urine stream collection chamber having a urine discharge opening and a urine stream collection opening, the urine stream collection opening having an edge being configured to surround and isolate a urethral opening;
providing a menstrual fluid passage having a menstrual fluid discharge opening and a menstrual fluid collection opening, the menstrual fluid passage being isolated from the urine stream collection chamber, wherein a portion of the menstrual fluid passage is defined by the edge of the urine stream collection opening forming an integrated interface configured for interior engagement with a vaginal opening;
inserting the integrated interface into the vaginal opening, effecting alignment of the urine stream collection opening with a urethra; and
providing substantially simultaneous passage through the menstrual fluid passage and urine stream collection chamber to effect discharge of the menstrual fluid from the menstrual fluid passage through the menstrual fluid discharge opening and discharge of urine from the urine stream collection chamber through one or more of the urine discharge opening and a spillway.

10. The method of claim 9, further comprising providing an internal baffle within the urine stream collection chamber that cooperates with at least urine sample container to provide the spillway to the discharge opening which provides urine passage out of the urine stream collection chamber.

11. The method of claim 9, further comprising providing a cap that engages with and closes off the discharge opening effecting a flow of urine through the spillway and out of the urine stream collection chamber.

12. The method of claim 9, wherein the alignment of the urine stream collection opening with the urethra occurs with the female standing or sitting in a reclined position, and discharge of urine from the urine stream collection chamber occurs with the female standing or sitting in the reclined position.

13. The method of claim 9, wherein the insertion of the integrated interface with the vaginal opening occurs with the female standing or sitting in a reclined position, and discharge of menstrual fluid from the menstrual fluid passage occurs with the female standing or sitting in the reclined position.

* * * * *